United States Patent [19]

Belliveau

[11] 4,173,974

[45] Nov. 13, 1979

[54] RESTRAINING MEANS

[76] Inventor: Robert J. Belliveau, 34 Ryder Rd. S., Weymouth, Mass. 02190

[21] Appl. No.: 835,063

[22] Filed: Sep. 21, 1977

[51] Int. Cl.[2] .............................................. A61F 13/00

[52] U.S. Cl. ........................................ 128/133; 70/16

[58] Field of Search .................. 128/133, 134; 119/96, 119/122; 70/16, 53

[56] References Cited

U.S. PATENT DOCUMENTS 2,645,922 7/1953 Martin ..................................... 70/16

*Primary Examiner*—Lawrence W. Trapp

*Attorney, Agent, or Firm*—Wolf, Greenfield, & Sacks

[57] ABSTRACT

A restraining device for individuals has an axially extending rigid support member. A first locking means acts to releasably engage handcuffs substantially at one end of the device and a second locking means acts to lock the device to a fixed location such as a vehicle floor. Keyless release levers for each locking means are located so as to be inaccessible to operation by the individual restrained.

Both the hands and legs of an individual are releasably connected to and restrained by a single rigid support member and the support member is releasably engaged with a predetermined mounting device in fixed position.

18 Claims, 8 Drawing Figures

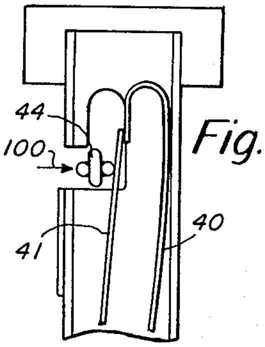
Fig. 4
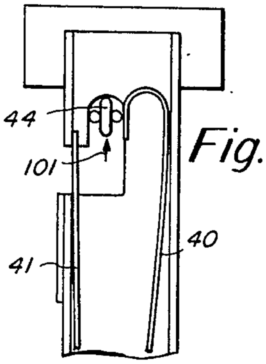
Fig. 5
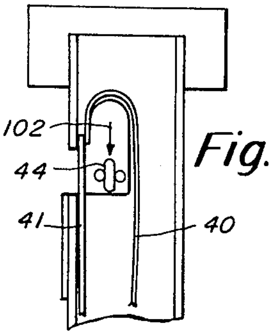
Fig. 6
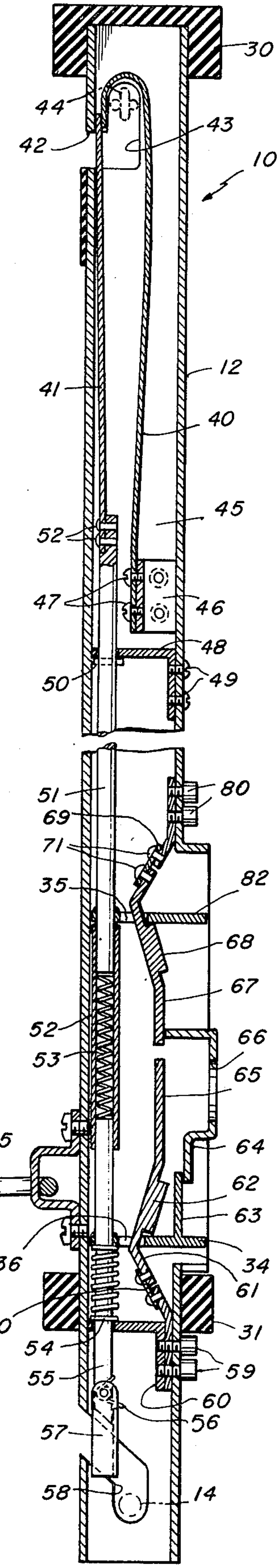
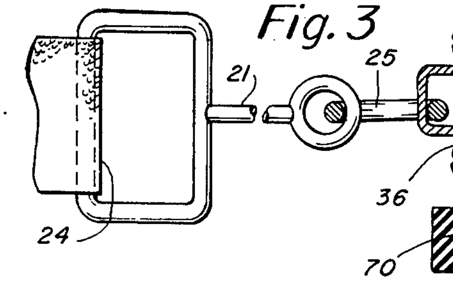
Fig. 3
Fig. 8
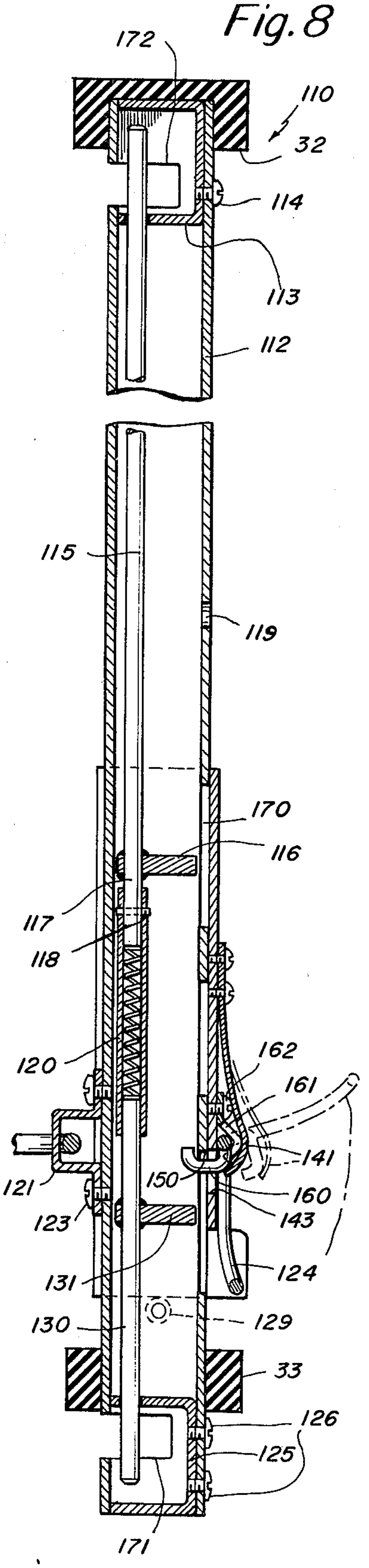

RESTRAINING MEANS

BACKGROUND OF THE INVENTION

Restraining devices for prisoners and the like are well known. Often handcuffs and feetcuffs are used for restraining arms and legs of individuals. However, such restraining devices are insufficient to fully immobilize an individual when being transported or left in particular locations for prolonged periods of time. For example, more restrictive devices are normally employed in connection with vehicles, interrogation rooms, cells, courtrooms and the like. In cars, often dividing screens are located between the prisoner and the driver while in interrogation rooms, more complicated cell devices are sometimes used. Often such devices require keylocks or combination locks which are difficult to quickly release in times of an emergency such as fire or other natural emergency requiring rapid release of the prisoner.

where simple handcuffs and legcuffs are used, it is often necessary to use two guards when transporting a prisoner. One guard normally sits next to the prisoner while another acts as a driver. This adds greatly to the cost of prisoner transport. In addition, the screens and other restraining devices known for use in motor vehicles, are quite costly. In addition to initial costs, such devices reduce the resale value of police cars and the like. When handcuffs alone are used, often a prisoner is handcuffed with his hands behind his back and then placed in a vehicle. The discomfort to the prisoner is obvious. In addition to physical discomfort, the prisoner in that position is unable to drink or smoke and is in a wholly unnatural position.

In addition to high cost, discomfort and the necessity for trained manpower in transport, the simple use of handcuffs allows some considerable movement of the prisoner and he is not tied to a fixed location.

SUMMARY OF THE INVENTION

It is an object of this invention to provide restraining devices for restraining individuals in predetermined locations which devices are positive restraints and are uncomplicated and economical to use.

It is another object of this invention to provide restraining devices in accordance with the preceding object which permit reasonable humane treatment of prisoners or other individuals while under restraint.

Still another object of this invention is to provide restraining in accordance with the preceding objects which devices can be keyless yet simple to operate by untrained personnel and substantially impossible for a prisoner to release even though no key need be used to lock or unlock the device.

Still another object of this invention is to provide humane devices in accordance with the preceding objects which devices are relatively inexpensive and permit significant cost saving in the transport and restraint of individuals.

Still another object of the invention is to provide restraining devices in accordance with the preceding objects which can be simply and rapidly released in time of emergency.

Still another object of this invention is to provide restraining devices in accordance with the preceding objects which can be used to restrain individuals for a wide variety of purposes such as prisoner restraints, restraints for individuals held in mental institutions, hospitals, courtrooms and the like.

According to the invention, a restraining device for retaining an individual in a predetermined location has an elongated axially extending rigid support member preferably with a length so that one end of the device is not accessible to the hands of an individual locked to the other end. A first means releasably locks a hand restraint device such as handcuffs at one end of the support. Second means releasably locks a second end of the support to a fixed location and a third means is provided for releasing the first means with said third releasing means not being accessible to the individual whose hands are restrained.

Preferably, second means are provided for restraining the feet of an individual and the second means is located between the first means and a second end of the axially extending rigid support member. Preferably, the means for locking the second end of the support to a fixed location is a releasable means so that the support member can be released while the hand and feet restraints are on a prisoner or other individual to be restrained and the device used when the individual is walking from one location to another.

In a preferred embodiment, the first means comprises a spring clamp means which has a double positive lock which lock is releasable by a finger action. The means for locking the second end of the support to a fixed location is preferably also released by a finger action. The finger activation levers used for release are inaccessible to the hands of the individual bound and to any other part of the individual that might be able to actuate the levers. Preferably double locks are used with positive stops so that two actions must be taken to release the individual from the support member.

In a second embodiment of the invention, a cover tube is used to positively cover the release mechanism for the device.

According to the method of this invention, an individual to be restrained has his hands releasably locked to an elongated rigid support member at one end thereof and his feet locked to the support member substantially at a second end thereof. The support member is then releasably attached to a stationary mounting whereupon the individual is restrained. After restraint for a required period, the individual is released by actuation of a first and second mechanism.

It is a primary feature of this invention that the device provides for secure restraint of individuals without the use of keys so that release can be quickly carried out in case of fire or other emergency. The restraint is movable with the individual from one location to another and aids in restraint of the individual both when moved in vehicles or when the individual is walked or carried without attachment of the restraint to a fixed support. The restraint is humane in that individuals can smoke, eat, drink and use toilet facilities even when harnessed to it. The individuals can be moved over long distances in relative comfort. The restraint can be used to attach to moving vehicles or to fixed locations such as the floor of cells, interrogation rooms, courtrooms and the like. The restraining devices of the invention are simple to operate by untrained personnel for rapid attachment and release. The restraint enables a single officer to transport prisoners. A single officer can handle one and/or more prisoners without the need for complicated and costly vehicle screens, cages and the like. The floor mounts for the restraints are inexpensive and can be mounted in a plurality of vehicles so that a single restraint has utility in a plurality of vehicles. Mounting of the floor mounts can be carried out simply by attaching a U-clamp to the floor of a vehicle requiring only the drilling of two holes. Such U-clamps can be removed from the vehicle with ease thus they need not reduce the resale value of vehicles. The restraining devices of this invention can easily be stored in the trunks of vehicles when not in use. Padding avoids injury to the prisoner in case of sudden stop or accident of moving vehicles.

BRIEF DESCRIPTION OF THE DRAWINGS

The above and other objects, features and advantages of the present invention will be better understood from a reading of the following specification in conjunction with the drawings in which:

FIG. 3 is a cross sectional view taken through line 3—3 of FIG. 2;

FIGS. 4–6 are detail views showing the operation of one preferred locking device of the preferred embodiment;

FIG. 8 is a cross sectional view taken through line 8—8 of FIG. 7.

BRIEF DESCRIPTION OF THE PREFERRED EMBODIMENT

Figure 1:
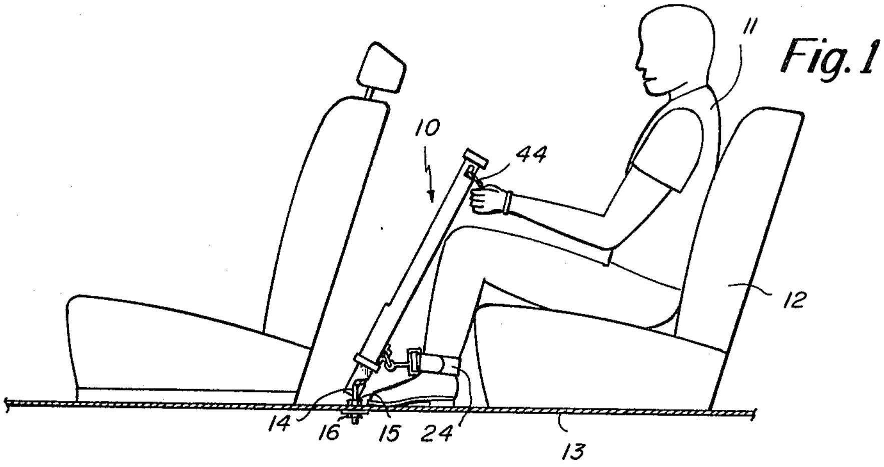
FIG. 1 is a cross sectional view through the cross section of a floor of a vehicle showing a preferred embodiment of the restraining device of this invention with an individual restrained in the device.
Figure 2:
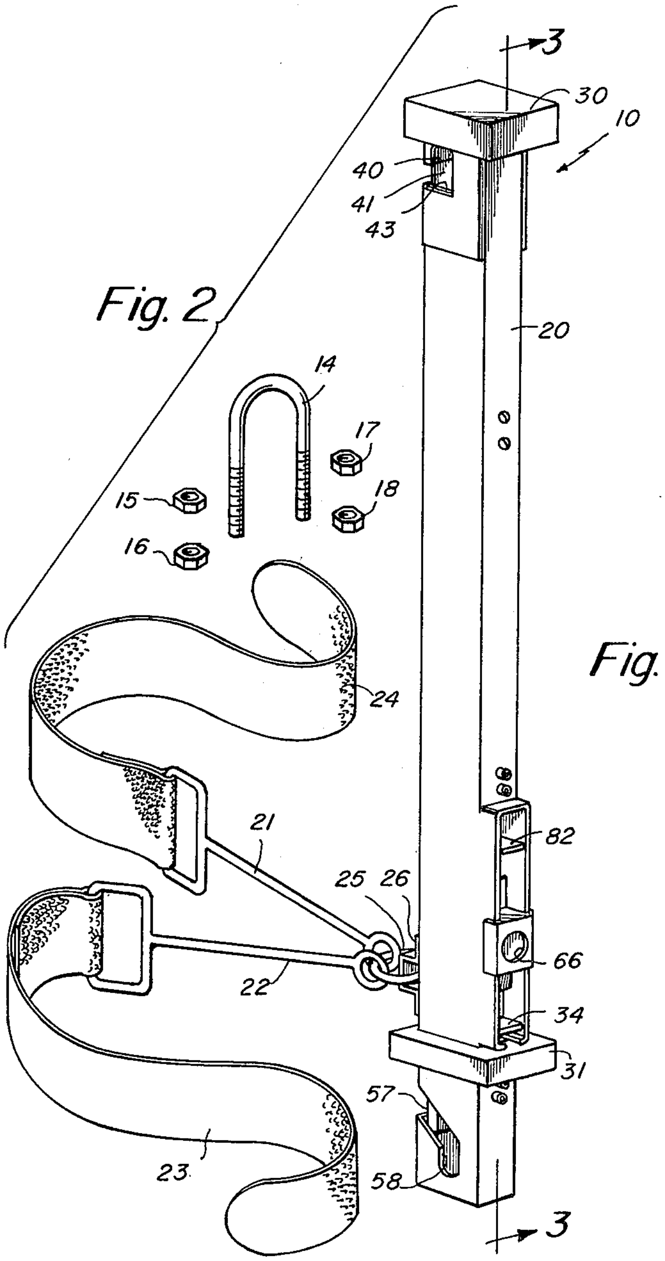
FIG. 2 is a perspective view of the restraining device of this invention showing an exploded section of the mounting device therefor.

With reference now to the drawings and more particularly, FIGS. 1–3, a preferred embodiment of a restraining device of this invention is illustrated generally at 10 mounted on the floor 13 of a vehicle (not shown) by a U-bolt support mount 14 affixed to the floor by two holes therein and nuts 15–18. The restraining device has an axially extending elongated rigid support member 20 with a first locking means acting through a cutout portion 43, a second locking means in the form of feet restraints 23 and 24, means for locking a second end of the restraining device to the U-bolt through cutout 58 and safety release means operable through cutout 66. The restraining device 10 is used in conjunction with conventional handcuffs illustrated at 44 holding the hands of an individual 11 seated on seat 12 as shown in FIG. 1.

The support member 20 is preferably a rigid steel rectangular tube. In the preferred embodiment, the tube has walls having a length of 1½" and two walls having a length of 1" about the circumference thereof. The length of the support member is such that the hands of the individual can be clamped to the notch 43 without the hands having access to the release means accessible at the second end of the device near the floor mount. This dimension is at least 12" and in the preferred embodiment, the support member has a length of 28" with the hand restraint notch 43 being located near the upper end.

The first means for releasably locking the chain of a handcuff has a band spring member 40 with a J-shaped upper end and a lower end mounted by screws 47 in fixed position on the support 20 through an angle iron 46 as best shown in FIG. 3. A second portion of the first locking means comprises a band or strip spring member 41 of spring steel similar to the steel of member 40 pinned by pins 52 to an elongated release rod 51. When the springs 40 and 41 are in the position shown in FIG. 3, a handcuff chain such as 44 cannot be removed from the notch 43 since the band spring member 41 bars the way as does member 40. To engage the handcuffs, the chain of the handcuff 44 is pushed against member 41 as best seen in FIG. 4 in the direction of arrow 100. A second step is necessary as shown in FIG. 5 which comprises movement in the direction of 101 to allow the band 41 to snap back and form a closure of the L-shaped slot 43. A second locking closure is formed by movement of the handcuff chain member downwardly in the direction of arrow 102 whereupon the spring 40 goes back to its original position. Thus, for the handcuffs to be removed when the spring members are in the position shown in FIG. 3, it would be necessary to move the spring 40. This spring is totally inaccessible from the outside of the support member. Release can only be accomplished by movement of the spring member 40 in a downward direction from the position shown in FIG. 3. This is accomplished through the rod 51. That rod is fixed to a cylinder 52 as by welding. Spring 53 exerts an upward force on the rod 51 and a downward force on a lower closure rod 55. The rod 51 has a stop pin 50 acting against a guide angle 48 mounted by screws 49 to the support member 20. The lower rod 55 has a spring 54 of greater strength than spring 53 thereby urging rod 51 constantly against the angle 48 while the rod 55 which is fixed to the upper end of the spring 54 is also urged upwardly against a stop 62. Angle 60 is mounted on the support 20 by screws 59. A release lever 82 is fixed as by welding to rod 51 with a second release lever 34 being affixed to the rod 55 for releasing that rod. Openings 35 and 36 provide for passage for the levers. The stops are substantially identical. Stop 68 comprises a raised portion on a steel strip attached through a spring 69 and pin 71 to a second portion of the stop pinned at 80 to the support 20. A finger gripping portion 67 of the stop can be depressed because of the spring action of spring 69 to release the lever 82 when it is desired to move the lever downwardly as shown in FIG. 3 to thereby release the upper locking means through downward movement of spring member 41 against the force of spring 53. It should be noted that a first action is required to depress the raised stop portion 68 resiliently whereupon the lever 82 can be used to release the handcuffs. Thus, a two-action release is provided.

The lower locking means to lock the device to the floor or other fixed location has a single release. Stop 62 is mounted on a strip of metal as previously described which is screwed to the support by pins 59 through an intermediate spring section 70 and provides a finger release portion 65. Depression of area 65 by a finger passing through hole 66 in a cover plate allows the lever 34 to be urged upwardly by spring 54 thus drawing the rod 55 upwardly and uncovering the lower substantially L-shaped slot 58 thereby allowing the U-bolt 14 to be withdrawn when desired.

The lower locking means is activated by merely snapping the U-bolt into position. This is accomplished by the U-shaped cross section dog 57 which is pivotally mounted on a spring loaded pin illustrated at 56. The spring loaded pin allows pivoting to open the slot 58 when a pressure is applied thereon. Once the U-bolt 14 is in location, pulling against the dog 57 will not open the slot. The slot can only be opened by actuation of the stop 62 as previously described.

The support member is preferably enclosed to prevent the prisoner or restrained individual from actuating the release mechanism except through predetermined locations such as hole 66. For this reason, closures of a small opened section can be carried out as by the use of wing portion 64 and an underlying wing 63 if desired. However, because of the location of the release, it is impossible for the individual to have his hands reach the release levers.

Feet restraints are preferably used with the device so as to prevent the prisoner from getting his feet into any position where the keyless releases can be activated.

Thus, in the preferred embodiment, a U-bracket 26 mounts rigid stirrup pieces 21 and 22 to which is attached Velcro leg restraints 23 and 24. Conventional Velcro pieces can be wrapped around an individual's legs as shown in FIG. 1 and positively restrain the legs. Moreover, since members 21 and 22 are rigid, the feet of the individual cannot reasonably get close enough to the opening for the release mechanisms to permit release of these mechanisms.

Preferably, rubber pads 30 and 31 are provided to cushion the device should the restrained individual collide with the device.

In use of the device, the dog 57 is pivoted back to admit the U-bolt 14 which is installed in the floor of a vehicle or stationary location as previously set forth. The prisoner can then be positioned on the seat with the handcuffs applied. The chain of the handcuffs is then moved through the positions shown in FIGS. 4 and 6 to attach the hands to the top of the device. The legs of the individual are then straped with the Velcro or other strap materials through the stirrups 21, 22 to lock the legs in position. It will be readily understood that quick release can be accomplished without the need for keys or trained personnel. Release is accomplished as previously described by depression of the stop 68 and movement of the lever 82 downwardly to release the hands. The feet can be released by release of the Velcro straps. More rapid release is carried out by simply releasing the U-bolt 14 by upward movement of the rod 55 and attached dog 57 caused by depression of stop 62 and automatic upward movement of lever 34. This releases the entire restraining device 10 from the fixed position while leaving the hands and feet of the individual restrained. The individual can walk with the device particularly if the Velcro leg bands are relocated to an uppermost position on the leg. Thus, a prisoner can walk to another location, such as a courtroom or toilet facilities when required. The same restraining device which restrains the individual when moving in a moving vehicle, also restrains him during walking and transport into and out of buildings. If U-clamps are used in stationary locations, such as courtrooms, the restraining device can be left on the individual, released from the vehicle and rapidly attached to a similar U-shaped device in the courtroom.

In an alternate embodiment of this invention, where fewer parts are used, restraining device 110 is shown having features basically similar to the features of the preferred embodiment. Thus, the elongated axially extending rigid support member 112 has an upper notch 172 and a lower notch 171. The first locking means is closed by a spring loaded rod 115 mounted in a spring tube 120 by a pin 118 and is welded at 117 to a release lever 116 passing through a guide hole provided by a U-shaped channel member 113 attached by screw 114 to the support member 112. The spring cylinder 120 containing a spring is biased against a lower rod 130 which mounts a release lever 131. A lower U-shaped channel member 125 is screwed to the support by screw 126 and has a guide hole passing therethrough. Additional fixed guide holes and mounts for the spring rod arrangement (not shown) may be used.

In this embodiment, a positive cover member in the form of cover tube 140 is used and slideably mounted on the support 112 so as to cover all access to release levers 131 and 116. A mounting bracket 121 mounts a spring loaded hook 122 by which feet handcuffs can be attached to the restraining device. In some cases, harness restraints of other types such as the leg restraints of the device 10 can be used in place of hook 122. Rubber bumper pads 32 and 33 are generally similar to pads 30 and 31 of device 10.

Figure 7:
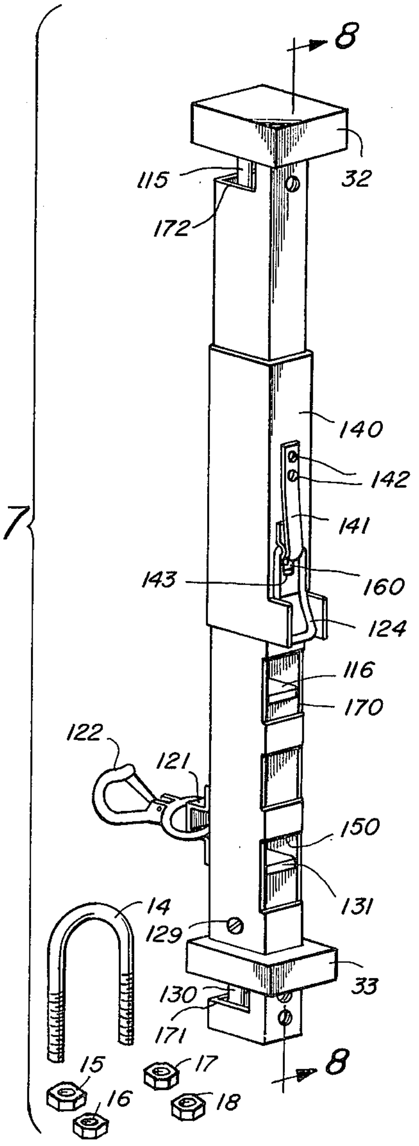
FIG. 7 is a perspective view of an alternate embodiment of this invention.

The cover 140 closes an opening 170 as well as opening 143 each of which provide access to the release levers 116 and 131. The cover has a bail 124 with a hook member 160 adapted to lock against an edge 150 in the closed position and interlock with a hole 119 when in the raised position of FIG. 7. The bail is constantly urged downwardly by a spring strip 141 attached to the cover by screws 142 and pivots within a holding clip 161 screwed to the cover by screws 162. The opened or released position of hook 150 is shown in phantom in FIG. 8 while its locked position is shown in full lines. FIG. 7 shows the locked upward position of the cover 140.

A stop pin 129 provides a limit for downward movement of the cover.

The restraining device 110 is somewhat shorter than restraining device 10 as for example being 22" in the preferred embodiment.

The device 110 is used in the same manner as the device 10. For example, the cover is placed in the raised position of FIG. 7. The hand of the user is used to depress rod 117 allowing entrance of the handcuff chain 44 thus locking handcuffs and attached hands to the top end of the device. The second end of the device is then attached to the U-bolt 14 by hand upward movement of lever 131. Release of the hand levers 116 and 131 automatically causes the rods 115 and 130 to lock in position locking the handcuffs and bolt 14 respectively in position. The cover is then slide downwardly by actuating the bail to its dotted line position of FIG. 8 and locked in position in the lowermost position. The feet of the individual to be restrained can be attached through the chain of handcuffs to hook 122. As before, release of lever 131 enables the device to be moved with the prisoner to another location different from the position defined by the U-bolt 14.

While specific embodiments of the present invention have been shown and described, many variations are possible. For example, the spacing between the handcuff locking means and the release mechanisms is such that the fingers of the restrained individual cannot release the device. Similarly, the feet are preferably maintained at a distance from the release buttons as by rigid stirrup members or cover means or the like are used to prevent the feet from activating the release mechanism. While a tube in rectangular form is shown for the support member, obviously, other rigid support shapes can be used. Similarly, padding of various types can be applied. The specific spring locking and release mechanisms are preferred although variations can be used. While it is preferred that the handcuffs be separate members, in some cases, handcuffs may be directly attached to the device. While a U-bolt is preferred for use with a rounded upper portion, other mounting brackets can be used if desired. The rounded rather than squared U-bolt is preferred in order to prevent the restrained individual from exerting any force on the bolt using the leverage of the support member. Thus, turning of the support about the bolt in any plane will not provide any substantial leverage to the user. An auxiliary cable can be attached to the lower locking means, as in notch 58 or 171 and in turn locked to a seat bottom of a train or plane where no preset U bolts are in place. The support member can have various cross sections other than rectangular but is always of a strong material such as 125 thousandths of an inch thick steel. In some cases, one or the other of the handcuff locking means or the U-bolt locking means can be permanent attachments although this is not preferred. For example, the means for locking the hands can be a weld or permanent bolt fixing handcuffs to the support 20, or the lower end of the support forming the means for locking the support to the floor, can be welded or permanently bolted to the floor. In either case, one of the means provides for rapid release by finger pressure and the means for release is inaccessible to the prisoner restrained. In all cases, there is a means for locking the hands to one portion of the support and a means for locking the support to a fixed location with at least one of the two means including a resiliently biased closure means so as to allow rapid release by finger pressure without the need for specific implements such as keys.

I claim:

1. A restraining device for retaining an individual in a predetermined location, said device comprising, a rigid support member having a length of at least twelve inches, first means for releasably locking a hand restraint device at one end of said support, means for releasably locking a second end of said support to a mounting means at a fixed location, means for releasing said first means with said releasing means being non-accessible to the individual whose hands are restrained, second means for restraining the feet of an individual with said second means being located between said first means and said second end, said support member being elongated and defining a cutout notch, said first means comprising a rod acting to close said notch to retain said hand restraint device or open said notch to allow release of said hand restraint device, said rod being spring loaded and having a lever for actuating opening of said notch.

2. A restraining device in accordance with claim 1 and further comprising said first means further comprising spring strips with one spring strip formed with a J shape and the second spring strip having a portion lying at a portion of said J to form a closed loop, said portion of said strip closing said J being located at an opening of said notch so that when an axially extending portion of said hand restraint is moved into said notch, said spring strips are both moved in a first direction, when said axially extending portion is then moved in a second direction, said loop opens and downward movement of said axial portion locks said axial portion within said loop and said support, said second strip acting to prevent removal of said axially extending portion in conjunction with said rigid support member, and means for moving said spring strip closing said loop out of a position blocking said opening whereby said hand restraint can be released when desired.

3. A restraining device in accordance with claim 2 wherein said second strip is attached to one end of said rod and said means for moving said second strip comprises said lever which acts to move said rod against spring bias, said lever being locked in position against release by a spring loaded stop whereby said stop must first be released before said lever can be moved.

4. A restraining device in accordance with claim 3 wherein said stop can be released by finger pressure at a point spaced from said notch by a distance greater than the reach of hands restrained by said hand restraint.

5. A restraining device in accordance with claim 3 and further comprising said means for locking the second end of said support comprising a second notch in said support member having a second spring loaded rod closing said second notch whereby said mounting means may be locked in said notch.

6. A restraining device in accordance with claim 5 and further comprising a second lever for actuating said second rod to release said mounting means, said second lever having a spring loaded stop whereby said stop must first be actuated before said second lever can be actuated to release said mounting means.

7. A restraining device in accordance with claim 6 and further comprising said mounting means being a U-shaped bolt attached to a position to which said restraining device is to be mounted.

8. A restraining device in accordance with claim 6 wherein said second means for restraining the feet of an individual comprises rigid stirrup portions having a length sufficient to prevent the feet of the user from having access to said levers of said restraining device.

9. A restraining device in accordance with claim 8 wherein said second means comprises rigid rods linked to said elongated support member and carrying Velcro straps for rapid attachment and release to the legs of an individual to be restrained.

10. A restraining device in accordance with claim 1 and further comprising said means for locking the second end of said support comprising a second notch in said support member having a second spring loaded rod closing said second notch whereby said mounting means may be locked in said notch.

11. A restraining device in accordance with claim 10 and further comprising a second lever for actuating the second rod to release said mounting means, said second lever having a spring loaded stop whereby said stop must first be actuated before said second lever can be actuated to release said mounting means.

12. A restraining device in accordance with claim 11 and further comprising said mounting means being a U-shaped bolt attached to a position to which said restraining device is to be mounted.

13. A restraining device in accordance with claim 12 wherein said rigid support member is an elongated hollow member with said rods positioned within said member and said member being opened at predetermined locations to permit actuation of said first means for locking said second end.

14. A restraining device for retaining an individual in a predetermined location, said device comprising, a rigid support member having a length of at least twelve inches, first means for releasably locking a hand restraint device at one end of said support, means for releasably locking a second end of said support to a mounting means at a fixed location, means for releasing said first means with said releasing means being non-accessible to the individual whose hands are restrained, said means for releasing said first means and said means for locking the second end of said support to a fixed location, are covered by an access cover which is movable to opened and closed positions.

15. A restraining device in accordance with claim 14 and further comprising second means for restraining the feet of an individual with said second means being located between said first means and said second end.

16. A restraining device in accordance with claim 15 and further comprising said support member being elongated and defining a cutout notch, said first means comprising a rod acting to close said notch to retain said hand restraint device or open said notch to allow release of said hand restraint device, said rod being spring loaded and having a lever for actuating opening of said notch.

17. A restraining device in accordance with claim 16 and further comprising said means for locking the second end of said support comprising a second notch in said support having a second spring loaded rod closing said second notch whereby said mounting means may be locked in said notch.

18. A restraining device in accordance with claim 17 wherein said rigid support member is an elongated hollow member with said rods and springs positioned within said member.

* * * * *